(12) United States Patent
Liu et al.

(10) Patent No.: US 9,683,253 B2
(45) Date of Patent: Jun. 20, 2017

(54) METHOD AND DEVICE FOR IDENTIFYING CELLS

(71) Applicant: IMEC, Leuven (BE)

(72) Inventors: Chengxun Liu, Leuven (BE); Willem Van Roy, Bierbeek (BE); Liesbet Lagae, Leuven (BE); Chengjun Huang, Leuven (BE)

(73) Assignee: IMEC, Leuven (BE)

(*) Notice: Subject to any disclaimer, the term of this patent is extended or adjusted under 35 U.S.C. 154(b) by 363 days.

(21) Appl. No.: 14/219,439

(22) Filed: Mar. 19, 2014

(65) Prior Publication Data
US 2014/0284221 A1 Sep. 25, 2014

(30) Foreign Application Priority Data
Mar. 19, 2013 (EP) .................................... 13159942

(51) Int. Cl.
| | | |
|---|---|---|
| *G01N 27/327* | (2006.01) | |
| *C12Q 1/04* | (2006.01) | |
| *G01N 15/10* | (2006.01) | |
| *G01N 27/02* | (2006.01) | |
| *G01N 33/487* | (2006.01) | |
| *B01L 3/00* | (2006.01) | |

(Continued)

(52) U.S. Cl.
CPC .......... *C12Q 1/04* (2013.01); *B01L 3/502761* (2013.01); *B03C 5/005* (2013.01); *B03C 5/026* (2013.01); *G01N 15/1031* (2013.01); *G01N 27/02* (2013.01); *G01N 33/48728* (2013.01); *B01L 2200/0652* (2013.01); *B01L 2300/0645* (2013.01); *B01L 2300/0816* (2013.01); *B01L 2300/0883* (2013.01); *B01L 2400/0424* (2013.01); *B03C 2201/26* (2013.01); *G01N 2015/0065* (2013.01)

(58) Field of Classification Search
CPC ...... G01N 27/02; G01N 33/427; G01N 15/12; G01N 15/87; G01D 5/24; C12M 35/02; C12N 15/87; C12Q 1/68; C12Q 1/04
See application file for complete search history.

(56) References Cited

U.S. PATENT DOCUMENTS

| | | | |
|---|---|---|---|
| 6,437,551 B1* | 8/2002 | Krulevitch | ......... G01N 33/5438 324/649 |
| 6,790,330 B2 | 9/2004 | Gascoyne et al. | |

(Continued)

FOREIGN PATENT DOCUMENTS

EP    2042239 A1    4/2009

OTHER PUBLICATIONS

Miltenyi Biotech, "Intracellular Staining of Eukaryotic Cells", http://www.miltenyibiotec.com/~/media/Images/Products/Import/0001200/IM0001205.ashx, pp. 1-4, retrieved Nov. 16, 2015.

(Continued)

*Primary Examiner* — Jennifer Dieterle
(74) *Attorney, Agent, or Firm* — McDonnell Boehnen Hulbert & Berghoff LLP (57) ABSTRACT

The present invention provides a method to analyze or identify a cell. The method comprises: providing a cell, stimulating the cell with a stimulant thereby modifying a cell membrane impedance of the cell, monitoring the cell membrane impedance of the cell and identifying the cell based on the monitored cell membrane impedance. A corresponding device is also provided.

16 Claims, 9 Drawing Sheets

(51) Int. Cl.
*B03C 5/00* (2006.01)
*B03C 5/02* (2006.01)
*G01N 15/00* (2006.01)

(56) References Cited

U.S. PATENT DOCUMENTS

| | | | |
|---|---|---|---|
| 7,033,473 B2 | 4/2006 | Gascoyne et al. | |
| 2005/0003396 A1* | 1/2005 | Ozkan | C12Q 1/6825 435/6.11 |
| 2005/0211557 A1* | 9/2005 | Childers | B03C 5/005 204/547 |
| 2006/0121446 A1* | 6/2006 | Abassi | C12M 35/02 435/4 |
| 2006/0210992 A1* | 9/2006 | van den Boom | C12Q 1/6883 435/6.12 |
| 2009/0096470 A1* | 4/2009 | Rabbitt | G01N 33/48728 324/693 |
| 2010/0068780 A1* | 3/2010 | Abonnenc | B03C 5/026 435/173.6 |
| 2010/0136699 A1* | 6/2010 | Drese | B01L 3/5027 436/43 |
| 2010/0259286 A1* | 10/2010 | Prodan | G01N 33/6872 324/692 |

OTHER PUBLICATIONS

Ratanachoo, Kanatip et al., "Detection of Cellular Responses to Toxicants by Dielectrophoresis", Biochim Biophys Acta., vol. 1564(2); Aug. 31, 2002, pp. 449-458.

Wang, Xujing et al., "Membrane Dielectric Changes Indicate Induced Apoptosis in HL-60 Cells More Sensitively Than Surface Phosphatidylserine Expression or DNA Fragmentation", Biochem Biophys Act., vol. 1564(2), Aug. 31, 2002, pp. 412-420.

Huang, Chengjun et al., "Electrokinetic Measurements of Dielectric Properties of Membrane for Apoptotic HL-60 Cells on Chip-Based Device", Biomed Microdevices, vol. 9, 2007, pp. 335-343.

Holmes, David et al., "Single Cell Impedance Cytometry for Identification and Counting of CD4 T-Cells in Human Blood Using Impedance Labels", Anal. Chem., vol. 82, No. 4, Feb. 15, 2010, pp. 1455-1461.

Manaresi, Nicolo, "A Workflow for Single-Cell Resolution, Automated, Image-Based Sorting of Pure Circulating Tumor Cells and Their Comprehensive Molecular Characterization", Silicon Biosystems, The Living-Cell Company, Molecular Medicine Tri-Conference, San Francisco, Feb. 21, 2012. 18 pages.

Inamoto, Naho et al., "Intermediate View Generation of Soccer Scene from Multiple Videos", IEEE 2002, pp. 713-716.

Doutre, Colin et al., "Color Correction Preprocessing for Multiview Video Coding", IEEE Transactions on Circuits and Systems for Video Technology, vol. 19, No. 9, Sep. 2009, pp. 1400-1405.

Brown, Duane C., "Decentering Distortion of Lenses", Presented at the Annual Convention of the American Society of Photogrammetry, Washington D.C., Mar. 1965 under the title "Decentering Distortion and the Definitive Calibration of Metric Cameras", pp. 444-462.

Yang, Ruigang et al., "Real-Time Consensus-Based Scene Reconstruction Using Commodity Graphics Hardware", 10th Pacific Conference on Computer Graphics and Applications, 2002, 10 pages.

Dumont, Maarten et al., "A Prototype for Practical Eye-Glaze Corrected Video Chat on Graphics Hardware", International Conference on Signal Processing and Multimedia Applications, 2008, 8 pages.

* cited by examiner

METHOD AND DEVICE FOR IDENTIFYING CELLS

CROSS-REFERENCE TO RELATED APPLICATIONS

This application claims the benefit of priority of European patent application no. 13159942.5, filed Mar. 19, 2013, which is hereby incorporated herein by reference in its entirety.

FIELD OF THE INVENTION

The invention is related to the field of cell identification and analysis. More specifically, the invention relates to a method and device for cell identification and sorting, suitable for oncological field.

BACKGROUND OF THE INVENTION

More than 90% of the cancer death cases are caused by cancer metastasis, where few tumor cells shed from primary tumor, circulate in the peripheral blood and finally dock and proliferate in another organ. The most effective approach for metastasis diagnosis is by the detection of circulating tumor cells (CTCs), so called "liquid biopsy". However, identifying a few CTCs amongst billions of blood cells is extremely challenging, as the CTC morphology is similar to those of blood cells, and due to the heterogeneity between CTCs.

It has been found that the electrical properties of tumor cells are different from that of normal blood cells. This difference in electrical properties is mainly due to the difference in cell membrane impedance, or in particular, in cell membrane capacitance. Multiple cancer cell lines have displayed a much higher membrane capacitance than normal blood cells. This finding brings the promise of isolating viable individual CTCs, which will enable further phenotyping and genotyping of CTCs, as well as improved clinical diagnosis and therapy.

As the whole cell membrane impedance is also dependent on cell size; measurement of absolute cell membrane impedance may lead to incorrect cell identification, as this cell size can be rather heterogeneous, especially for cancer cells. For example, a big monocyte may have the same cell membrane impedance as a small cancer cell.

So there is a need for a method to identify CTC's in blood using cell impedance measurements with a high efficiency and accuracy.

SUMMARY OF THE INVENTION

In a first aspect of the invention, a method to analyze or identify a cell is presented. The method comprises: providing a cell, then stimulating the cell with a stimulant thereby modifying a cell membrane impedance of the cell, thereafter monitoring the cell membrane impedance of the cell and then identifying the cell based on the monitored cell membrane impedance.

It is an advantage of certain embodiments of the present invention that the response of the cells to the stimulant allows an accurate method of cell identification. It is a further advantage of certain embodiments of the present invention that multiple cells have a different response for the same stimulus, so different types of cells may be identified in one measurement.

According to certain particular embodiments of the invention, the cell may be provided in a fluid.

It is an advantage of embodiments of the present invention that sample handling is improved while increasing cell mobility.

According to certain embodiments of the invention, monitoring the cell membrane impedance comprises measuring a crossover frequency of the cell by applying at least one electrical field, characterized by at least one non-zero frequency, which creates a dielectrophoretic (DEP) force on the cell. The crossover frequency of the cell is the frequency at which the cell experiences zero DEP force.

It is an advantage of certain embodiments of the present invention that cell determination can be obtained from a measurement of a DEP force depending on mass, membrane responsiveness to stimulant and impedance, hence increasing the accuracy of cell determination.

According to certain embodiments of the invention, applying the electrical field of at least one non-zero frequency comprises varying the frequency of the electrical field. It is an advantage of certain embodiments of the present invention that the measurement can be done continuously and fast.

According to certain embodiments of the invention, applying an electrical field comprises applying electrical fields with different frequencies. This allows the measurement to be done accurately, and cell separation may be facilitated.

According to certain embodiments of the invention, the measurement of a crossover frequency of the cell is repeated. It is an advantage of certain embodiments of the present invention that accuracy is increased and the possibility of errors reduced.

According to certain embodiments of the invention, monitoring of the cell membrane impedance comprises performing a direct electrical impedance measurement. According to certain embodiments of the invention, the direct electrical impedance measurement is done using electrochemical impedance spectroscopy. According to certain embodiments of the invention, performing the direct electrical impedance measurement is repeated.

It is an advantage of certain embodiments of the present invention that monitoring and cell determination may be less time consuming. It is a further advantage that use can be made of electrochemical impedance spectroscopy.

According to certain embodiments of the invention, identifying the cell comprises correlating the monitored cell membrane impedance with predetermined cell membrane impedance measurements of a cell.

It is an advantage of certain embodiments of the present invention that use can be made of look-up tables and models, which can be used for performing correlation with predetermined cell membrane impedance measurements which also may comprise predetermined cell membrane capacitance density and cell membrane conductance density of cells, as well as crossover frequency measurements.

According to certain embodiments of the invention, the cell is provided in a fluid with a predetermined electrical conductivity and measuring a crossover frequency of the cell is repeated for at least one different fluid, the at least one different fluid having a different electrical conductivity to determine a membrane capacitance density and a membrane conductance density. The identification of the cell is further based on the determined membrane capacitance density and membrane conductance density.

It is an advantage of certain embodiments of the present invention that different response times to stimulus of different samples can be compensated for by measuring the impedance under the same frequency, measurement time and electric field, but by changing the variable of the fluid conductance. It is an advantage of certain embodiments of the present invention that capacitance may be directly obtained from the cross-over frequency Fc measurement of the same sample with different fluids. It is an advantage of certain embodiments of the present invention that capacitance may be measured by changing the fluidic medium, in cases in which the sample may be less sensitive to changes of frequency within the range of the experiment. It is a further advantage of certain embodiments of the present invention that by determining the cell membrane capacitance density and the cell membrane conductance density, the identification of the cell can be done more precisely, thereby creating a more sensitive technique to identify cells.

In a second aspect of the invention, a method for sorting cells is presented. The method comprises: providing a fluid comprising at least one cell, identifying a type or subtype of the at least one cell as described in any embodiment of the first aspect of the invention and sorting the at least one cell based on the identified type or subtype.

It is an advantage of certain embodiments of the present invention that cell sorting may be performed in an accurate manner, effective and with only few errors. It can be done in a manner which is only little time consuming.

In a third aspect of the invention a micro-fluidic device for identifying cells is presented. The device comprises: at least one inlet, at least one outlet, a micro-fluidic channel comprising a plurality of electrodes positioned along the micro-fluidic channel, one end of the micro-fluidic channel is connected to the at least one inlet and the other end of the micro-fluidic channel is connected to the at least one outlet. An electric power supply unit is connected to the plurality of electrodes. The plurality of electrodes comprises at least two groups of electrodes. Each group of electrodes is connectable to at least one electric power supply unit capable of providing at least one voltage of at least one non-zero frequency. The electric power supply supplied to a first group of electrodes has a different frequency than the electric power supply supplied to a second group of electrodes.

It is an advantage of certain embodiments of the present invention that cell monitoring of impedance or DEP of a stimulated cell can be done for different fluids, or can be done simultaneously for different frequencies and fields depending on the electrode between which the cell is situated, the position being determined for instance by implementation or by flow of a fluid.

According to certain embodiments of the invention, the micro-fluidic device may further comprise a processing unit suitable for performing a correlation on data. The correlation may be performed between the monitored cell membrane impedance and pre-defined cell membrane impedance models. The pre-defined cell membrane impedance models may be stored in a database comprising pre-defined cell membrane impedances of cells.

According to certain embodiments of the invention, the micro-fluidic device may further comprise a means for redirecting cells connected to the at least one outlet for sorting cell based on type or subtype.

It is an advantage of certain embodiments of the present invention that redirecting means may be comprised in the processing unit. It is a further advantage of certain embodiments of the present invention that separation of cells may be provided, depending on their type, to at least one of a plurality of outlets.

According to certain embodiments of the invention, the micro-fluidic channel features a meander-like shape. This provides a device which is compact and consumes little space.

In a further aspect, the present invention provides the use of a micro-fluidic device according to any of the embodiments of the third aspect of the present invention for identifying and/or sorting cells.

DETAILED DESCRIPTION OF THE INVENTION

Throughout the text, the wording "monitoring" may be interpreted as "measuring" or "determining" a given magnitude, for example continuously measuring the magnitude over a pre-determined amount of time, for example measuring the magnitude at regular time periods during a particular time window, for example 3 hours or less, for example 25 minutes. For example, monitoring may be interpreted as measuring a given magnitude while changing a controllable parameter. "Monitoring a cell membrane impedance" may be interpreted as "measuring one or more cell membrane impedances" or "determining one or more cell membrane impedances", for example "measuring one or more cell membrane impedances during a pre-determined amount of time", for example "measuring one or more cell membrane impedances for a variable value of a controllable parameter". In certain particular embodiments of the present invention, the impedance may be measured for a given period of time. In the same or other embodiments of the present invention, the impedance may be measured for a range of controllable frequencies of an applied electrical field.

Throughout the text reference is made to "a cell" or "cells" which refers to a biological cell or biological cells.

Throughout the text reference is made to "cell type". A cell type is a classification used to distinguish between morphologically or phenotypically distinct cell forms within a species. Within each cell type, one or more "cell subtypes" may be defined.

Throughout the text reference is made to "predetermined monitored cell membrane impedance measurements" which refers to "monitored cell membrane impedance measurements which is already obtained", for example a set of membrane impedance measurements obtained in a different experiment.

Throughout the text reference is made to sweeping an electric field frequency which refers to varying the frequency of the electric field.

Throughout the text reference is made to "cell sorting", which refers to the action of separating cells according to their properties.

Throughout the text, reference is made to "direct electrical impedance measurement", which refers to a direct impedance measurement, rather than to determination of impedance based on alternative measured values.

In the context of the present invention, a technique based on dielectrophoresis (DEP) is applied, which is a phenomenon in which a force is exerted on a dielectric particle suspended in a non-uniform electric field. The electric field polarizes the particle, and the poles then experience a force along the field lines, which can be either attractive or repulsive according to the orientation on the dipole. Since the field is non-uniform, the pole experiencing the greatest electric field will dominate over the other, and the particle will move. The strength of the force depends strongly on the medium and the particles' electrical properties, on the particles' shape and size, as well as on the frequency of the electric field.

In this invention, a technique for cell identification and analysis is disclosed. The technique uses cell membrane impedance measurements to identify cells. The properties of the membrane of a cell can be influenced by stimulating the cell chemically. During such stimulation, the cell membrane physically changes which in turn modifies the cell membrane impedance. The inventors have determined that a cell membrane recovers after it is stimulated with particular stimulants. As the cell membrane recovers, the cell membrane impedance changes. When measuring the cell membrane impedance over time, the measurement results reflect the response of the cell to the stimulus. It was surprisingly found that the response of the cell to the stimulus over time is different for different cell types or cell subtypes. The specific response of the cell to the stimulation enables analysis or identification of cells. Further, the results of identification of cells may be used to e.g. sort cells.

Figure 1:
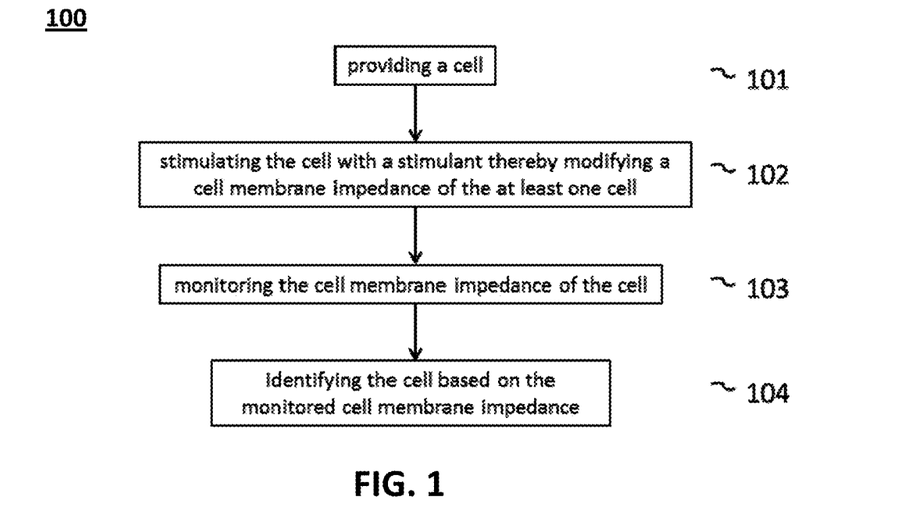
FIG. 1 illustrates a block diagram of a method to identify cells.

In a first aspect of the invention, a method to identify cells is presented. The method is illustrated with a block diagram of FIG. 1. The method comprises providing 101 a cell to be analysed, identified and/or sorted, which may be a healthy cell or a tumor cell. A second step comprises stimulating 102 the cell with a stimulant thereby modifying a cell membrane impedance of the cell. Thereafter the cell membrane impedance of the cell is monitored 103 and the cell is identified 104 based on the monitored cell membrane impedance. The cell may or may not be presented in a fluid. The cell is stimulated with a stimulant (e.g. a chemical stimulant, or a toxin, the present invention not being limited thereto) thereby modifying a property of the cell membrane of the cell. As a result, the cell membrane impedance of the cell is different after stimulation than before. After stimulating the cell with the stimulant and/or after removing the stimulant, the cell membrane impedance is monitored for a pre-determined period of time (e.g. a plurality of cell membrane impedance measurements are done, or continuous impedance measurement is done; until the pre-determined period of time has elapsed, or until a pre-determined result is obtained). By analyzing the monitored cell membrane impedance, the cell can be identified. This analysis may encompass comparing the monitored cell membrane impedance with predetermined monitored cell membrane impedance measurements of a cell. This can be done e.g. by using a look-up table. The comparison may be performed by correlating the monitored cell membrane impedance with predetermined monitored cell membrane impedance measurements of a cell. The predetermined monitored cell membrane impedance measurements of a cell may comprise data of different types or subtypes of cells.

According to certain embodiments of the invention, the cell membrane impedance may be monitored by performing direct electrical impedance measurements, which may be repeated to ensure a correct result. The direct electrical impedance measurements may be performed using electrical impedance spectroscopy using micro electrode arrays or any other suitable technique such as patch clamp, the present invention not being limited by these examples.

Cell membrane properties such as the cell membrane impedance are related to the crossover frequency of a cell. The crossover frequency of a cell is the applied frequency at which the DEP force on the cell is equal to zero. The DEP force or dielectrophoretic force refers to the interaction between a non-uniform electrical field applied to physical object and the electrical dipole moment created by that electromagnetic field in that physical object. The membrane or the intracellular structure of a cell is regarded as being damaged if the crossover frequency or the electric property of the cell deviates from the native value by at least a predetermined value. According to certain embodiments of the invention, to monitor cell membrane impedances, the crossover frequency of each cell may be measured multiple times over a given period of time.

According to one embodiment of the invention, each time the crossover frequency of a cell is measured, the measurement may be performed at least twice to correct for possible incorrect measurements.

Figure 5:
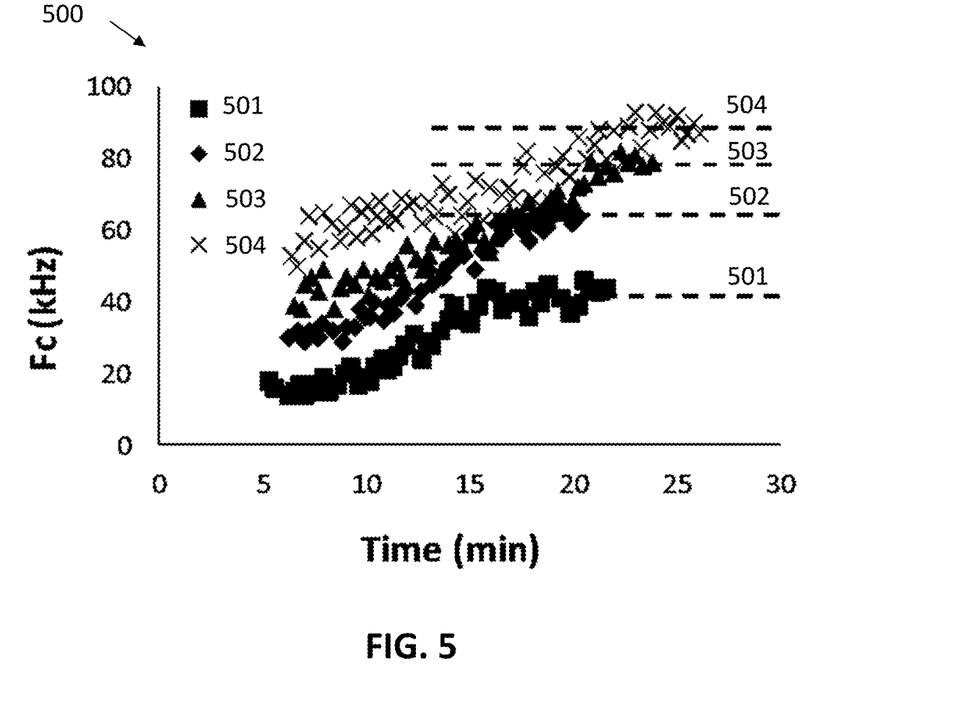
FIG. 5 illustrates the PBMC response to trypsin treatment. Trypsin concentration was 0.002 M (¹/₂₅ dilution). The dashed line indicates the native Fc value.

FIG. 5 illustrates a diagram 500 showing the crossover frequency Fc of Monocytes 501 (represented as a square), NK cells 502 (diamond), B cells 503 (triangle) and T cells 504 (cross) measured over time after a Trypsin stimulation. The Trypsin concentration was 0.002 M (1/25 dilution). The crossover frequency Fc for each cell was measured over a period of 20 to 25 minutes at predetermined intervals. The dashed lines indicate the native Fc value for each cell type. After 20 to 25 minutes it is noticed that the crossover frequency reaches the native Fc value of respectively a Monocyte 501, NK cell 502, B cell 503 or T cell 504. It is thus noticed that the cell membrane recovers from the stimulant.

Figure 14:
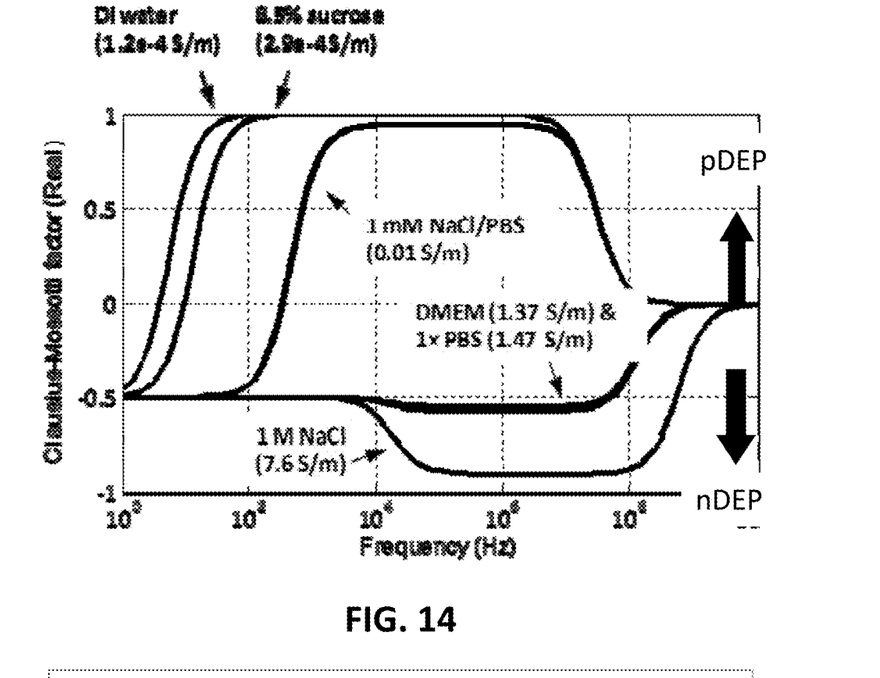
FIG. 14 illustrates the relation between the Clausius-Mossotti factor and the frequency of the applied electrical field

Each crossover frequency is measured by applying a DEP force on a cell and by determining the frequency at which the cell experiences zero DEP force. The DEP force is created by applying an electrical field at certain frequency, e.g. an AC electric field. Alternatively, different electrical fields may be applied subsequently, each being characterized by a different frequency. The signal may comprise a sine wave, or square wave, triangle or trapezoidal wave, or a pulsed signal, for instance a pulse-width modulated signal, or any other suitable signal, the present invention not being limited thereof. For any wave used wave shape, it can be at single frequency or mixed. The frequency of the electrical field can vary from for example (the present invention not limited thereto) 100 Hz to 50 Mhz, e.g. from 1 kHz to 10 Mhz for a particular medium conductivity. FIG. 14 illustrates the relation between the Clausius-Mossotti factor and the frequency of the applied electric field for different media. The frequency dependence and the direction of the DEP force are governed by the real part of the Clausius-Mossotti factor. If the particle, e.g. cell, is more polarizable than the medium, the particle, e.g. cell, is attracted to high density electric field regions. This is called positive dielectrophoresis (pDEP). If the particle, e.g. cell, is less polarizable than the medium, the particle, e.g. cell, is repelled from high intensity field regions and negative dielecrtrophoresis (nDEP) occurs. As illustrated in FIG. 14, the real part of the Clausius-Mossotti force characterizes the frequency dependence of the DEP force. The DEP crossover frequency Fc is the transition frequency point where the DEP force $F_{DEP}$ switches from pDEP to nDEP or vice versa. It is possible to vary the frequency of the applied field to obtain measurements, and additionally it may also be possible to vary the medium (for instance, using fluids with different conductivity) to obtain different measurements.

DEP is the movement of electrically polarized objects as a function of frequency of the electric field, for instance the movement of a polarized object in an AC electric field. The object is actuated by the Coulomb force if the electric field is spatially non-uniform. The determination of the DEP force $F_{DEP}$ may be modelled according to Eq. 1, where w is the angular frequency of the electric field, R the cell radius, d the cell membrane thickness, $\pounds_m$ is the permittivity of the medium, E the electric field, $f_{CM}(\omega)$ the Clausius-Mosotti (CM) factor (Eq. 2), $\pounds^*_{ICM}$ the complex permittivity for intracellular matrix (ICM) and $\pounds^*_{MEM}$ the complex permittivity for cell membrane. This is often called protoplast model. When the DEP force $F_{DEP}$ is positive, the cell is attracted to the electrode and vice versa. The frequency at which $F_{DEP}$ is zero, is named crossover frequency Fc.

$$F_{DEP} = 2\pi R^3 \varepsilon_m \mathrm{RE}[f_{CM}(\omega)] \nabla E^2 \quad \text{(Eq. 1)}$$

$$f_{CM} = \frac{\varepsilon^*_{cell} - \varepsilon^*_m}{\varepsilon^*_{cell} + \varepsilon^*_m} \quad \text{(Eq. 2)}$$

$$\varepsilon^*_{cell} = \varepsilon^*_{mem} \frac{\left(\frac{R}{R-d}\right)^3 + 2\left(\frac{\varepsilon^*_{icm} - \varepsilon^*_{mem}}{\varepsilon^*_{icm} + 2\varepsilon^*_{mem}}\right)}{\left(\frac{R}{R-d}\right)^3 - \left(\frac{\varepsilon^*_{icm} - \varepsilon^*_{mem}}{\varepsilon^*_{icm} + 2\varepsilon^*_{mem}}\right)} \quad \text{(Eq. 3)}$$

Figure 4:
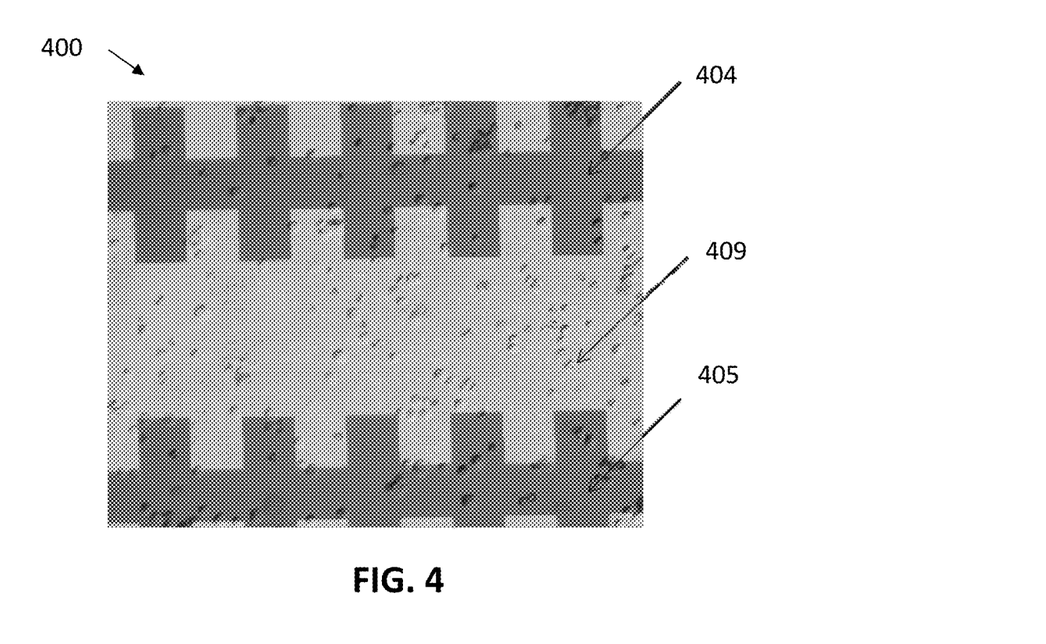
FIG. 4 illustrates a microfluidic channel with two electrodes for performing DEP measurement.

A state of the art device 400 is shown in FIG. 4 where an electric field is applied across two co-planar Au electrodes 404, 405, for the analysis of the movement of cells 409. In practice, Fc may be measured by monitoring the cell movement when sweeping the excitation electric field frequency. Alternatively or additionally, Fc may be measured by monitoring the cell movement for various electric fields characterized by different frequencies. Fc is identified when the cell stops moving, neither being attracted to nor repelled from the electrodes.

According to an embodiment of the invention, the electrical property of cells may be calculated from multiple Fc measurements for different medium (fluid) electrical conductivities. Preferably different fluids may be used, each fluid characterized by a different electrical conductivity. Following the protoplast theory, Fc can be solved through Eq. 2 when the real part of $f_{CM}$ is zero. Thus Eq. 4 is obtained, where C is membrane capacitance density (F/m$^2$) and G the membrane conductance density (S/m$^2$), i.e. the capacitance and conductance per unit area of cell membrane.

$$\mathrm{Re}(f_{CM}) = 0 \Rightarrow F_c = \frac{1}{2\pi RC}\sqrt{(\sigma_m - RG)(2\sigma_m + RG)} \quad \text{(Eq. 4)}$$

If multiple Fc's are measured for different medium conductivities, the values of C and G can be determined by Eq. 5 and 6, respectively.

$$C = 1/(\sqrt{2}\pi R \cdot dF_c/d\sigma_m) \quad \text{(Eq. 5)}$$

$$G = \sigma_{m,itcp} \quad \text{(Eq. 6)}$$

To identify or analyze cells, monitored cell membrane impedance can be compared to predetermined cell membrane impedance measurements (e.g. by using look-up tables). These predetermined measurements may have been obtained in a previous different experiment. The monitored cell membrane impedance may be correlated with predetermined cell membrane impedance measurements. The predetermined cell membrane impedance measurements may be e.g. a library containing cell membrane impedance measurements of different types of cells. The comparison may be done by a processing device, for example a microprocessor, and the library, lookup table and such may be stored in a memory, although the present invention is not limited thereto. The monitored cell membrane impedance of the cell under investigation is correlated to the predetermined cell membrane impedance measurements of different types of cells. If there is a correlation between the monitored cell membrane impedance of the cell under investigation and predetermined cell membrane impedance measurements of a particular type of cell, the cell under investigation can be identified.

According to certain embodiments of the invention, by monitoring the DEP crossover frequency for different fluid conductivities, the cell membrane capacitance density and the cell membrane conductance density can be determined (according to eq. 5 and eq. 6). The identification of the cell may be further based on the determined cell membrane capacitance density and the cell membrane conductance. It is advantageous to measure a plurality of crossover frequencies for different fluid conductivities as, according to eq. 5 and eq. 6, this enables the determination of the cell membrane capacitance density and the cell membrane conductance density. By determining the cell membrane capacitance density and the cell membrane conductance density, the identification of the cell can be done more precisely thereby creating a more sensitive technique to identify cells. In order to identify cells, a correlation can be performed with predetermined cell membrane impedance measurements which also may comprise predetermined cell membrane capacitance density and cell membrane conductance density of cells.

According to one embodiment of the invention, the identification of the cell under investigation may comprise identifying a cell type or subtype of the cell under investigation. It is an advantage of certain embodiments of the invention that different cell subtypes can be identified. This is enabled by the analysis of the response of a cell to a stimulus, e.g. a chemical stimulus.

According to one embodiment of the invention, the identification of the cell under investigation based on cell membrane impedance measurements of the cell may comprise identifying a response of the at least one cell to the stimulant. The identification may be performed by checking a match between a cell response pattern and a pre-defined cell response model.

According to one embodiment of the invention, the changes of the dielectric property of a cell may be used to evaluate the effectiveness of the stimulant to the cell and hence to the host biological entity from whom the cell was extracted. As such, the analysis of the cell based on the monitored cell membrane impedance of the at least one cell may be used for the purpose of a drugs and analysis means drug response.

According to one embodiment of the invention, the cell under investigation may be subjected to different types of stimulants. The analysis or identification of the cell may then be performed by comparing the cell membrane impedance measurements of the cell for different stimulants. As an advantage, the cell membrane impedance measurements of the cell for different stimulants can be used to analyze and understand which effects each stimulant has on the cell under investigation. This analysis can be used for drug testing purposes (compare against positive and negative controls).

Different embodiments of the method according to the present invention may be combined. For instance, the direct measurements of impedance may be combined with Fc measurements for unambiguous cell determination.

In a second aspect of the invention, a method to sort cells is presented. A fluid comprising at least one cell to be sorted is provided. The fluid may contain cells of different types or subtypes. The method to identify cells as described in embodiments of the first aspect of the invention is used to identify the at least one cell, and preferably each cell, present in the fluid. After the cells have been identified, the cells are sorted according to the identified cell type or subtype. Cell sorting refers to actuating (e.g. leading) cells to different fluidic outlets depending on the cell identification. The actuation force can be the DEP force itself or other forces such as acoustic force, optical force, magnetic force (in certain embodiments, the cells may be responsive to magnetic fields, for instance if the cells are labelled with magnetic beads), or fluidic flow (when the system is equipped with fast valves). Sorting may also include, for instance, labelling of cells, or separation.

In a third aspect of the invention, a micro-fluidic device for identifying or analyzing cells is presented. The device comprises multiple regions which may be used to identify or analyze cells in accordance with embodiments of the present invention. Such regions may be DEP regions. A DEP region is a region of the micro-fluidic channel which comprises electrodes allowing to apply an electrical field to a cell thereby creating a DEP force on the cell. The device may be e.g. a micro-fluidic chip.

Figure 2:
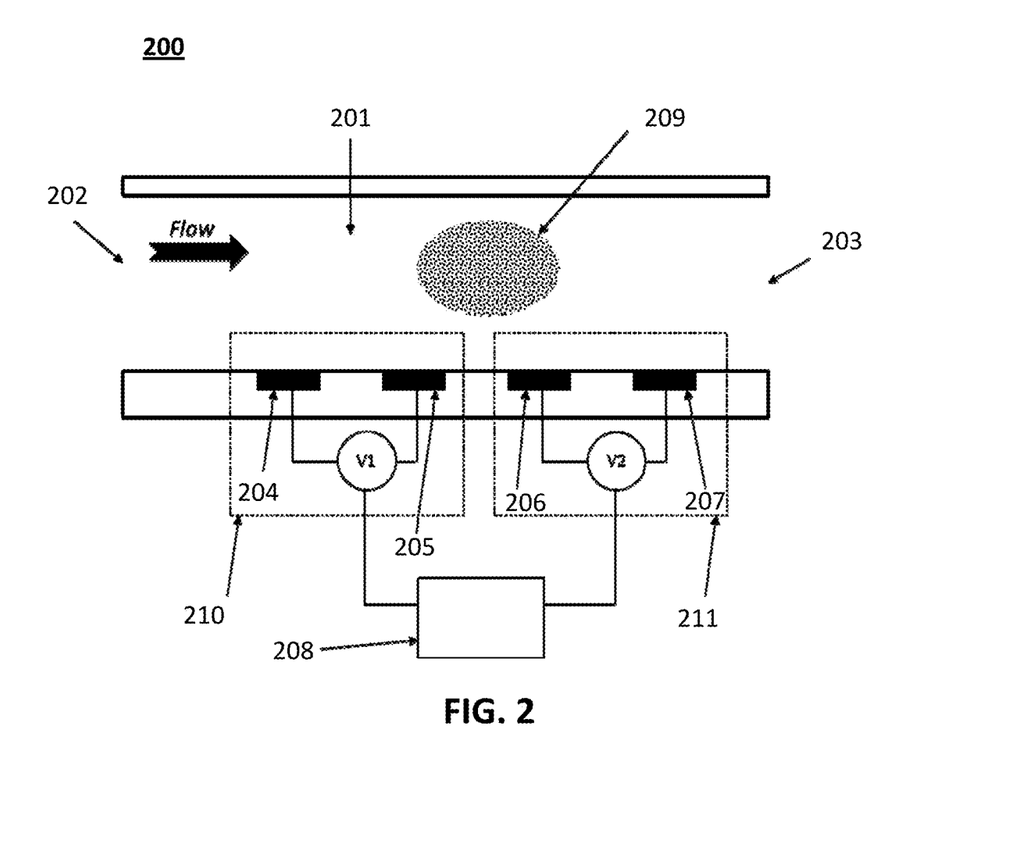
FIG. 2 illustrates a micro-fluidic device with two DEP regions.

FIG. 2 illustrates a cross-section of an embodiment of a device 200 according to embodiments of the present invention comprising two regions suitable for DEP measurement (DEP regions) 210,211. The device 200 comprises a micro-fluidic channel 201 which at one end has an inlet 202 and at the other end has an outlet 203. The device further comprises four electrodes 204, 205, 206, 207. The electrodes 204, 205, 206, 207 may be fully or partly embedded in a surface of the micro-fluidic channel 201. The electrodes 204, 205 of the first DEP region 210 are connected to an electric power supply V1 which supplies an electric power supply voltage with a first frequency. The electrodes 206, 207 of the second DEP region 211 are connected to an electric power supply V2 which supplies an electric power supply voltage with a second frequency.

According to one embodiment of the invention, the electrodes in each DEP region 210, 211 are connected to an electric power supply. The number of electric power supplies may be equal to the number of DEP regions. In one DEP region all electrodes are connected to an electric power supply. In another DEP regions, all electrodes are connected to another electric power supply. Different electric power supplies may generate electric power supply voltages with different frequencies, hence in the embodiment illustrated the first frequency and the second frequency differ from one another. Each electric power supply may generate an electric power supply voltage. The signal provided by the power supply may be AC, pulsed (for instance pulsed DC), or a current providing a series of harmonic frequencies, the present invention not being limited thereto.

According to another embodiment, all electrodes in the micro-fluidic channel 201 may be connected to an electric power supply unit 208 for generating electric power supply voltages with different frequencies for each DEP region 210, 211. Each electric power supply unit 208 may generate AC electric power supply voltages with different frequencies.

A fluid comprising a cell 209 is provided in the micro-fluidic channel 201. A first DEP force is created by electrodes 204, 205 in the micro-fluidic channel 201. A second DEP force, different from the first DEP force, is created in the micro-fluidic channel 201 by electrodes 206, 207. Thus, the device contains 2 different DEP regions, in each region a different electrical field is present. A cell 209 which passes through the micro-fluidic channel 201 is subsequently influenced by both DEP regions 210, 211. Using different DEP regions, different crossover frequencies of the cell 209 can be determined. When a cell membrane is recovering from a stimulant, different DEP regions can determine different crossover frequencies of the same cell at different moments in time as the cell is flowing through a micro-fluidic channel 201 with the different DEP regions 210, 211. Different DEP regions can also determine a (fixed) crossover frequency of different types of cells (e.g. in the situation where cells are not stimulated and the crossover frequency of the cells does not change). If the DEP force of a DEP region 210, 211 on the cell is equal to zero, the crossover frequency of the cell can be determined.

As described in the first aspect of the invention, cells 209 are stimulated with a stimulant thereby modifying the cell membrane impedance. As the cell membrane recovers from this stimulant, the cell membrane impedance changes. This change results in a different crossover frequency of the cell over time. The device as presented in embodiments of the third aspect of the invention may be used to determine the crossover frequency change of a single cell over time while flowing through the micro-fluidic channel.

Figure 3:
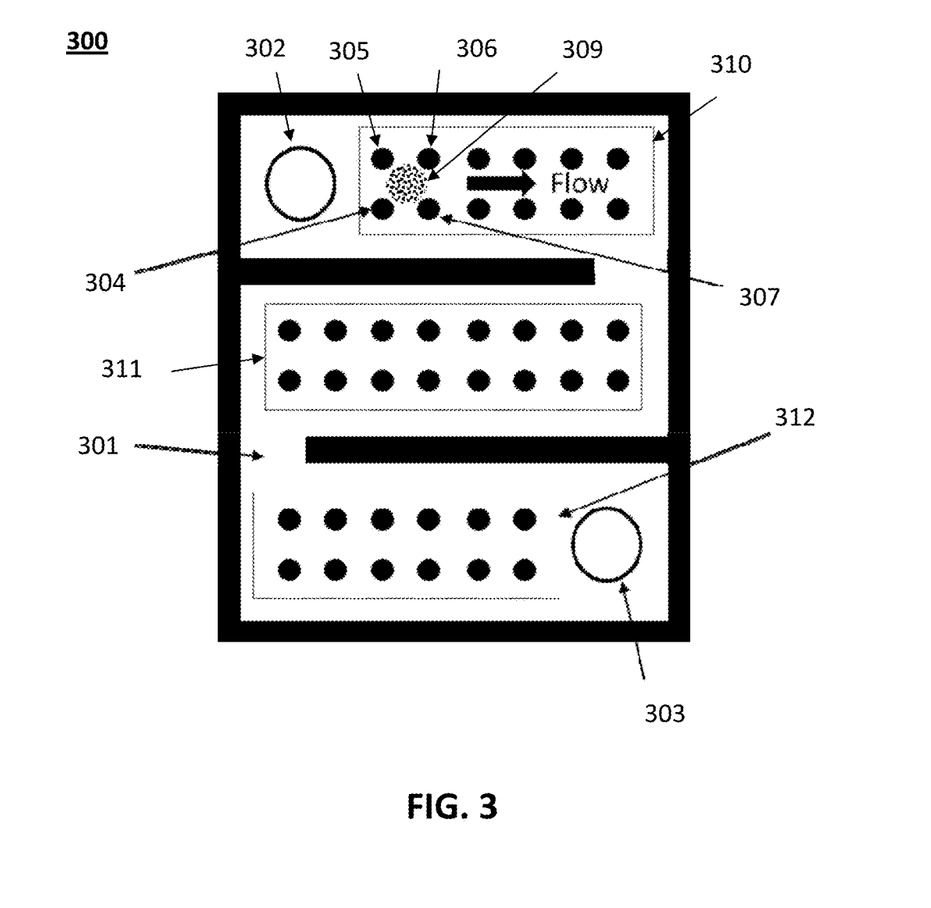
FIG. 3 illustrates a micro-fluidic device with three DEP regions.

FIG. 3 illustrates a top view of a device 300 according to one embodiment of the invention comprising three DEP regions 310, 311, 312. The device 300 comprises a micro-fluidic channel 301, an inlet 302 for providing or receiving a fluid comprising a cell 309, an outlet 303 for exiting the fluid comprising the cell 309 and a plurality of electrodes 304, 305, 306, 307. The micro-fluidic channel 301 has a meander-like shape. As an advantage, the device is more compact. The micro-fluidic channel 301 comprises an inlet 302 at one end of the micro-fluidic channel 301 and an outlet 303 at the other end of the micro-fluidic channel 301. The electrodes are positioned between the inlet 302 and the outlet 303. The electrodes are positioned along the micro-fluidic channel 301 and are positioned in 3 DEP regions 310, 311, 312. Each DEP region 310, 311, 312 comprises a group of electrodes. Each electrode of an electrode group of a DEP region 310, 311, 312 is connected to a power supply voltage with a different frequency. An electric power supply unit (not illustrated in FIG. 3) may generate power supply voltages with different frequencies for each group of electrodes of the DEP regions 310, 311, 312.

According to one embodiment of the invention, the micro-fluidic device 300 may comprise more than one inlet, allowing e.g. insertion of different fluids and/or more than one outlet, allowing e.g. sorting of cells.

When a fluid comprising a cell 309 is provided to the device 300 as illustrated in FIG. 3, the cell 309, when passing through the channel 301, will be influenced by three different DEP regions 310, 311, 312 wherein each region 310, 311, 312 applies a different DEP force on the cell 309. Each region 310, 311, 312 may be used to determine the crossover frequency of the cell 309. As an advantage, the device may be used to identify different types of cells as each DEP region 310, 311, 312 can determine the crossover frequency of a particular cell.

A device comprising three DEP regions 310, 311, 312 can be used to determine the crossover frequency of three types or subtypes of cells. Thus, in this case the device can identify 3 different types or subtypes of cells.

When cells are stimulated with a stimulant, the electrical impedance of the cell 309 changes while the cell 309 is recovering from the stimulation. The electrical impedance of the cell 309 changes continuously until the cell 309 has fully recovered from the stimulation. The device 300 may be used to monitor the cell impedance change by measuring the crossover frequency of the cell 309 at different moments in time using multiple DEP regions 310, 311, 312 as the cell 309 flows through the micro-fluidic channel 301.

A first DEP region 310 may be used to determine a first crossover frequency. As a cell membrane recovers from the stimulant, the cell membrane impedance changes. This change implies that the DEP force on a cell 309 in the first DEP region 310 is not equal to zero anymore, thus, the cell 309 will flow through the micro-fluidic channel 301 to the second DEP region 311 where a second crossover frequency can be determined. As the cell membrane is further recovering, the cell membrane impedance changes which enables the cell to flow to a third DEP region 312 which may determine a third crossover frequency. The device 300 may comprise an electric power supply unit (not illustrated) which generates power supply voltages with different frequencies for different DEP regions. The different DEP regions may be used to monitor the crossover frequency of a cell 309. It is advantageous that standard electric components can be used to implement the device, e.g. the electric power supply unit.

According to one embodiment of the invention, the micro-fluidic device 300 may further comprise a processing unit (not illustrated) suitable for performing a correlation to identify cells. The processing unit may be capable of performing a correlation between determined crossover frequencies of a cell and pre-determined crossover frequencies of a cell. The processing unit may comprise a processor, e.g. a microprocessor, and a memory wherein the memory may store look-up tables with pre-determined crossover frequencies of cells, e.g. an erasable electronic programmable readable-only memory (EEPROM).

According to one embodiment of the invention, the device may further comprise a means for redirecting identified cells to a determined direction, e.g. to an outlet, to sort the cells. The means for redirecting cells may be a microfluidic switch which redirects particular identified cells to an outlet. The processing unit may be adapted for controlling the means for redirecting cells. If the micro-fluidic device 300 comprises a plurality of outlets, the means for redirecting cells may be used to redirect identified cells towards one of the plurality of outlets.

According to an embodiment of the invention, the micro-fluidic device 300 may further comprise a means for propagating a fluid sample comprising cells through the micro-fluidic channel 301. The means for propagating a fluid sample may be a pump, e.g. a capillary pump.

In the paragraphs below experimental results are presented.

Experimental Results

Cells

For the examples, multiple cell lines were chosen, shown in Table 1. They were cultured using standard cell culture practice, but also other types of cell cultures may be used. In this particular example, the culture was split twice a week by making use of a Trypsin 0.05% (Sigma-Aldrich). The remaining culture was kept in the exponential growing phase by adding new cell culture medium which resulted in a cell density of around $10^6$ cells/ml.

TABLE 1

| Cell line name | Tumor origin |
| --- | --- |
| MCF7 | Breast cancer cell line |
| MDA-MB-231 | Breast cancer cell line |
| LnCap | Prostate cancer cell line |
| SKOV3 | Ovarian cancer cell line |
| HEK | Human kidney cell line |

Fresh blood samples, which may be provided by healthy donors, were also used for some experiments, for instance as control samples. For these particular examples, the blood was collected in a blood collection tube with EDTA as anticoagulant. This was followed by density gradient centrifugation (20 min, 2000 RCF). Prior to centrifugation the citrate in the tube was removed as EDTA was already preventing coagulation.

The buffy coat, containing the peripheral blood mononuclear cells (PBMCS) was collected after centrifugation and stored in serum at room temperature for a maximum of 12 hours.

To fix the PBMCs, 1 mL buffy coat was centrifuged at 300 g for 10 minutes. After aspiration of the supernatant, the cells were re-suspended in a mixture of 250 µl (microliters) PBS and 250 µl (microliters) insider Fix (Miltenyi Biotech) and incubated for 20 min at room temperature. After fixation, the cells were centrifuged and washed for two times with the buffer used for DEP crossover measurements. Finally, the cells were re-suspended in the DEP buffers for DEP measurements at different medium conductivity.

Chemical Stimulation of Cells

To determine the response of the different types of cells to chemical stimulants, three different stimulants were used for this study: Trypsin, Triton X-100 (TX100) and toxins. Cell stimulants were added into DEP measurement medium (a medium having a conductivity of e.g. 98 μS/cm, mixture of sucrose and NaCl) to achieve target concentration. Trypsin concentrations between 0.0005 M and 0.05 M were used. For Triton X-100, only a 0.01% (v/v) solution was used. Two pore-forming toxins were used: Streptolysin-O (SLO) and alpha-toxin of *S. aureus*. Different toxin concentrations were tested: 0.01, 0.1, 1 and 10 μg/ml (micrograms per milliliters).

Cells were first collected and incubated with solutions of different stimulant concentrations for one minute at room temperature. After incubation the mixture was centrifuged, followed by replacement of the supernatans with 0.5 ml of measuring medium with a conductivity of 98 μS/cm. This washing step was repeated three times in total to completely remove the stimulant from the medium. The DEP measurement immediately followed afterwards. Alternatively, direct impedance measurement may be performed.

Measurement of the DEP Crossover Frequency (Fc)

Effects on the dielectric properties of the cells were evaluated by measuring the crossover frequency Fc with predetermined medium conductivity. In this example (the present invention not limited thereto), the amount of 100 μl (microliters) of the cell suspension was introduced directly onto the electrodes on the measurement device. An alternating electric field was applied to a pair of opposing coplanar electrodes on the device. The DEP force may be generated and varied by the introduction of a series of electric fields with different frequencies. Alternatively, in the case of the present example, the frequency of the electric field was adjusted during the experiment and the corresponding movement of the cells studied. Depending on the frequency, and thus the DEP force, the cells moved away or towards the edge of the electrode. The transition from a repulsive force to an attractive force occurs at the crossover frequency at which the cells do not move. During some experiments the crossover frequency was observed over a period of time. For those experiments the period of time was started at the moment the stimulant was removed.

Direct Measurement of the Cell Impedance

The cell impedance, e.g. cell membrane capacitance and conductance, can also be directly measured by on-chip electrodes, e.g. by using electrodes 304, 305 present in the micro-fluidic channel (as shown in. FIG. 3). The impedance may be measured when the cell flows over the electrodes where there may or may not be close contact between the cell 309 and any of the electrodes 304, 305, 306, 307. Alternatively, the impedance measurement can also take place when the cell contacts at least one of the electrodes.

The Electrical Property of Cells without Stimulation

Figure 6:
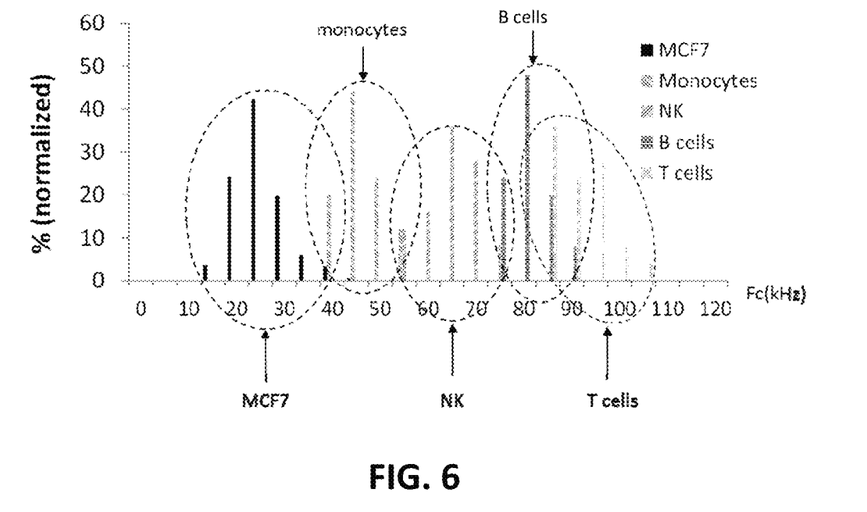
FIG. 6 illustrates the crossover frequency Fc of MCF7 cells and typical leukocytes.

The crossover frequency of tumor cells and major portion of PBMCs, i.e. monocytes, natural killer, B- and T-cells were measured (monitored) to find their respective Fc, in medium conductivity of 98 μS/cm, shown in FIG. 6. The different types of leukocytes were pre-sorted by fluorescence-activated cell sorting (FACS). An overlap between the Fc of MCF-7 and monocytes can be observed.

Figure 7:
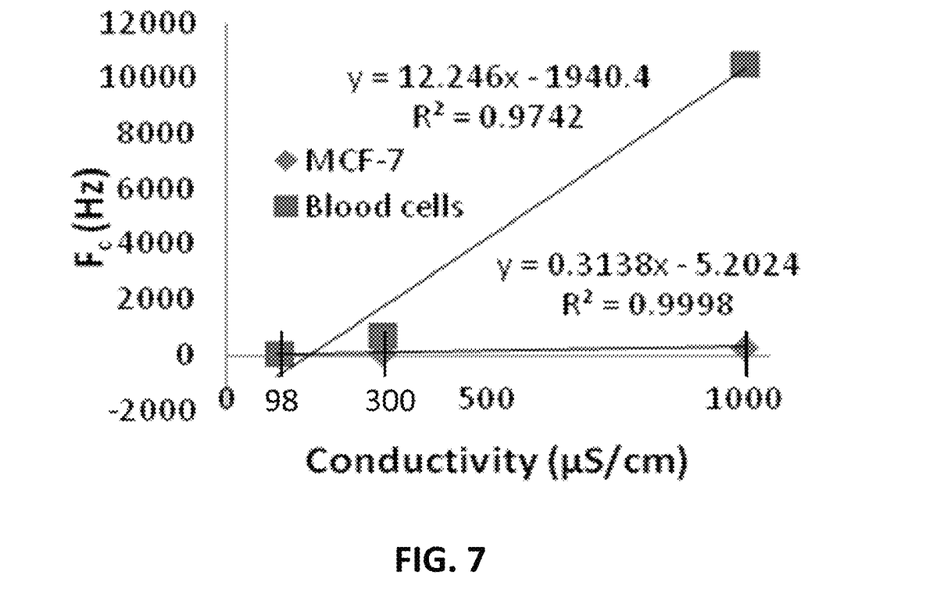
FIG. 7 illustrates the effect of medium conductivity on crossover frequency Fc of MCF7 and PBMC.

The Fc was further measured at multiple medium conductivity (FIG. 7). At higher medium conductivity, the Fc for both cancer cells and normal leukocytes was higher, same for the contrast. This finding agrees very well with Eq. 4. Also indicated by FIG. 7, when the medium conductivity is sufficiently higher than that of the cell membrane, Fc was indeed almost a linear function of medium conductivity $\sigma_m$. This implies that Eq. 5 & 6 are valid in this regime.

Figure 8:
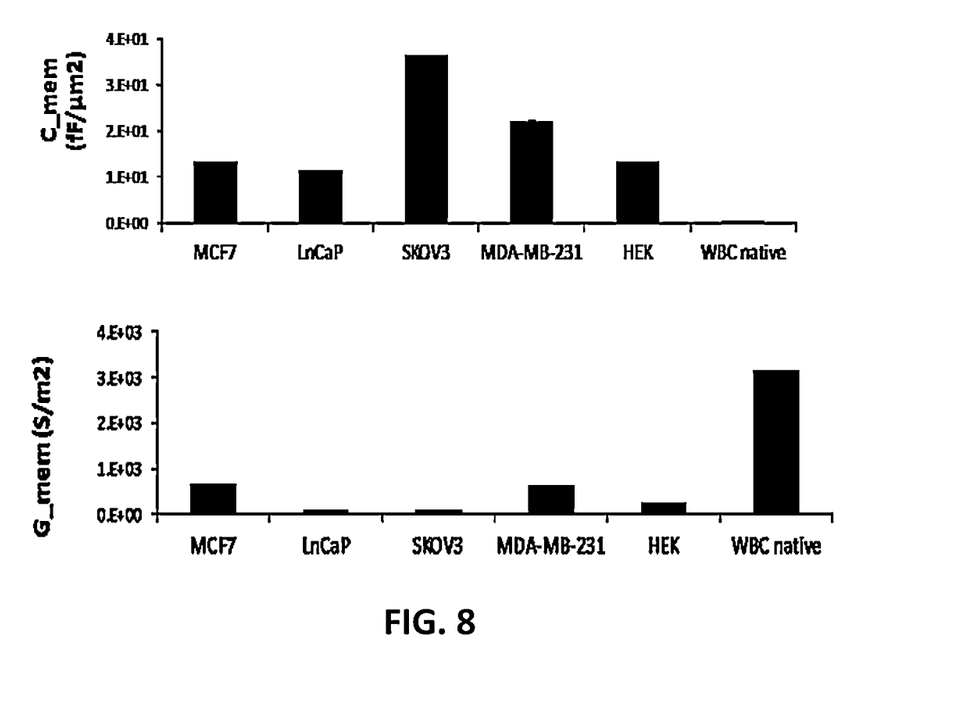
FIG. 8 illustrates the membrane capacitance (top) and conductance (bottom) for tumor cells and white blood cells.

The same experiment was repeated for multiple cancer cell lines, and their membrane capacitance and conductance were extracted by Eq. 5 & 6 (FIG. 8). Clearly, tumor cells exhibit higher membrane capacitance and lower membrane conductance than white blood cells. Thus, tumor cells can be distinguished from white blood cells by measuring their absolute membrane capacitance and conductance.

Effect of Cell Fixation on DEP Crossover Frequency

Figure 15:
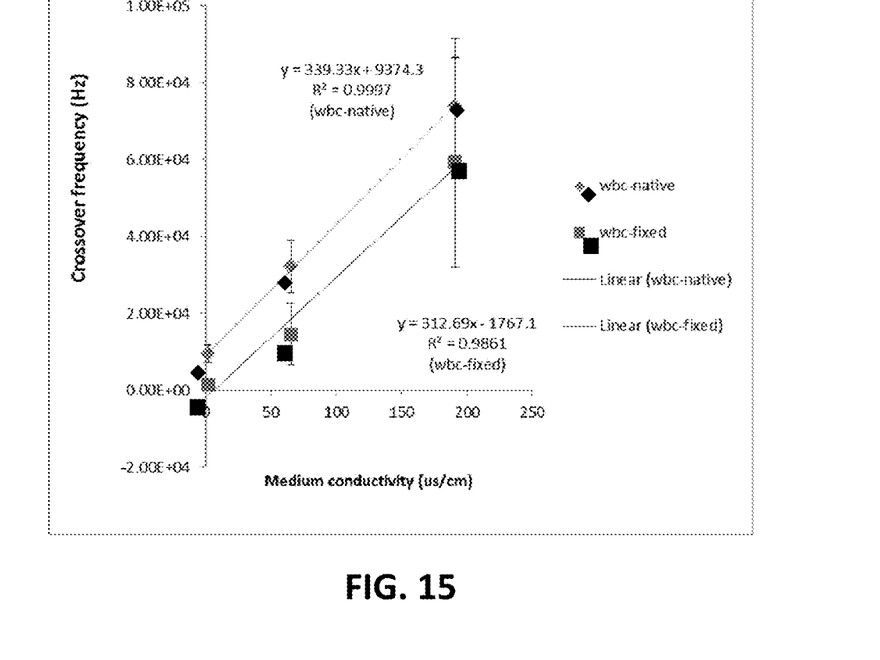
FIG. 15 illustrates the crossover frequency Fc of PBMC before and after fixation
Figure 16:
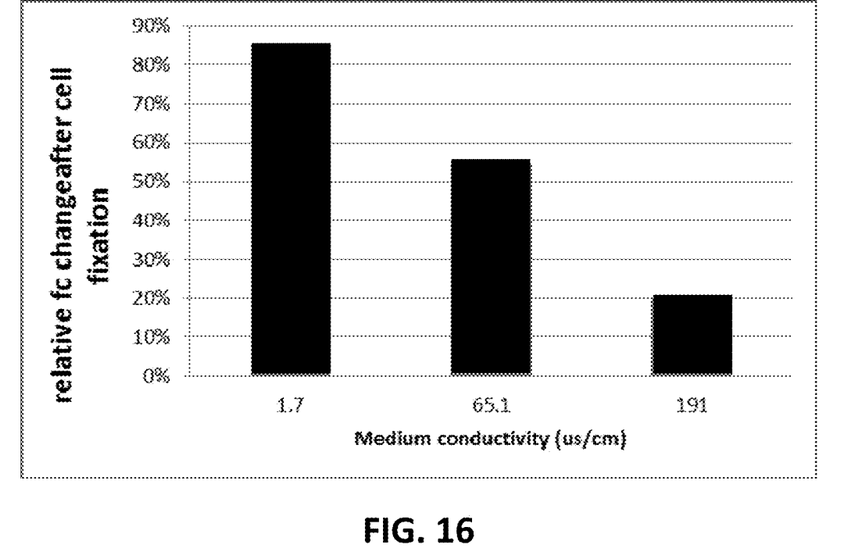
FIG. 16 illustrates a comparison of the relative change of crossover frequency Fc of PBMC before and after fixation

In the present example, different methods comprising fixation, for instance staining, may be followed, the present invention not being limited thereto. The crossover frequency of PBMCs before and after fixation following the commercial "inside fix" procedure (Inside Fix being a product from Miltenyi GmbH, see http://www.miltenyibiotec.com/~/media/Images/Products/Import/0001200/IM0001205.ashx, with core material being formaldehyde), the present invention not being limited thereto, was also measured to evaluate the effect of cell fixation on the crossover frequency in multiple medium conductivities, as shown in FIG. 15. Although after the cell fixation, the averaged crossover frequencies slightly decreased for all 3 measured medium conductivities, the linear correlations between Fc and medium conductivity remain for the PBMCs with and without fixation. The slopes of two linear correlations for PBMCs before and after fixation have not shown significant change at the measured condition. From FIG. 16, it can also been seen that the variation of the cross over frequency after fixation was within the range of 100%, which was almost the same range of the standard deviation for the individual cells at the same condition.

Cell Stimulation by Trypsin

Figure 9:
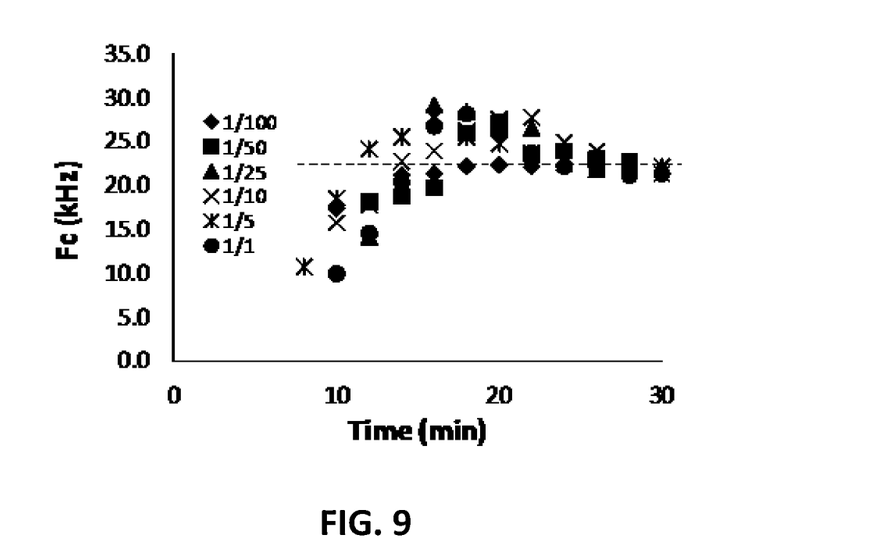
FIG. 9 illustrates crossover frequency Fc of MCF7 cells after trypsin stimulation. Undiluted Trypsin concentration (1/1) was 0.05 M. The dashed line indicates the native crossover frequency Fc value.
Figure 10:
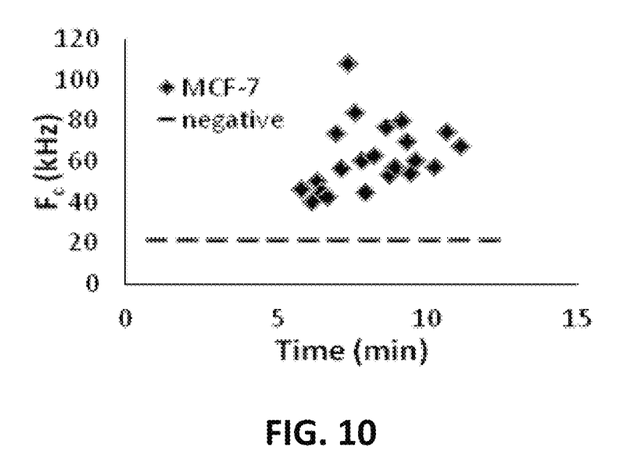
FIG. 10 illustrates Fc of MCF7 cells after alpha toxin incubation. The dashed line indicates the native Fc value.
Figure 11:
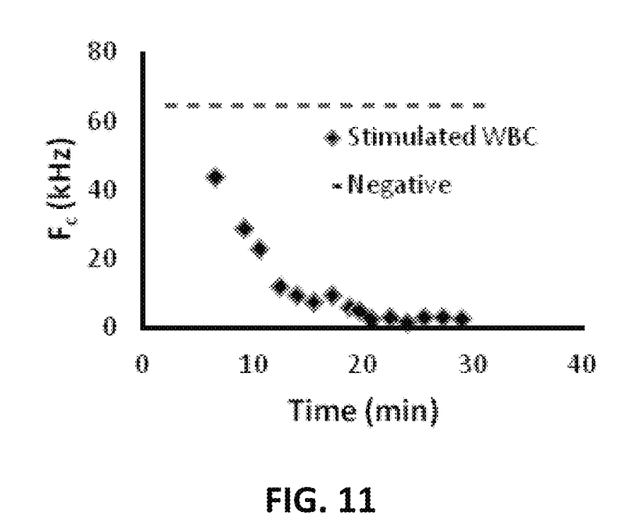
FIG. 11 illustrates Fc of white blood cells after alpha toxin incubation. The dashed line indicates the native Fc value.
Figure 12:
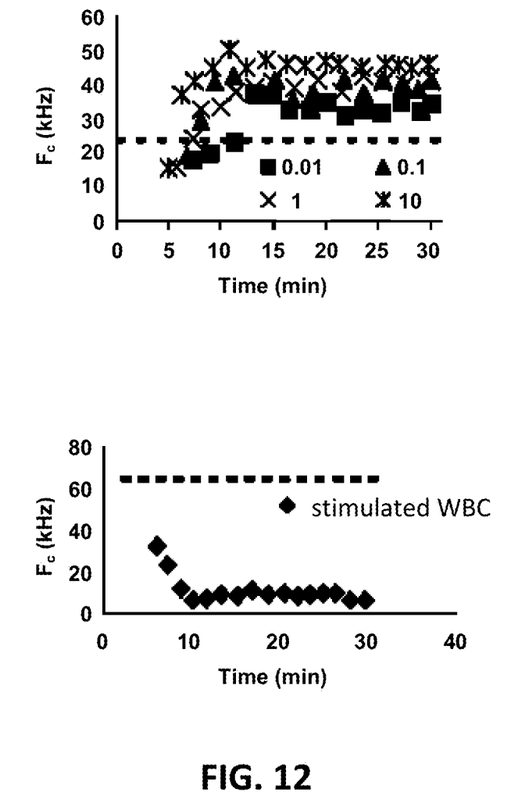
FIG. 12 illustrates the Fc recovery from SLO stimulation.
Figure 13:
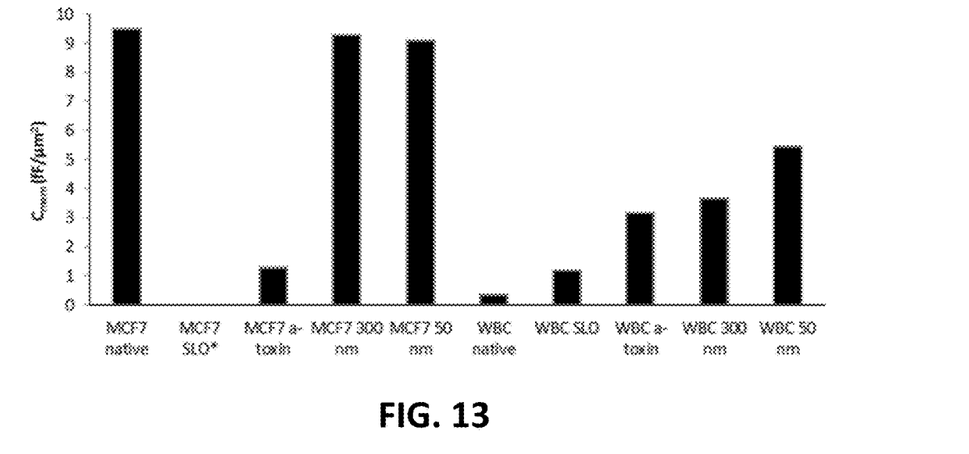
FIG. 13 illustrates the impact of cell stimulation on cell membrane capacitance.

Trypsin is a widely used pancreatic enzyme. It digests membrane proteins and thus changes the membrane impedance. When the Trypsin concentration is low (as used in the following experiments) the cell membrane may spontaneously recover after Trypsin removal. This can be found from both the Fc recovery of MCF7 cells and leukocytes, shown in FIG. 9 and FIG. 5. However, the Fc recovery of MCF7 cells was not monotonic, i.e. the value of Fc first develops a higher value than the non-stimulated (native) value and then drops back to the native value. By contrast, the Fc recovery of leukocytes was always monotonic. Thus, cancer cells can be distinguished from blood cells by measuring the recovery trend. This particular method belongs to one embodiment of the present invention, the present invention not being limited to this feature. Moreover, this feature is not limited to a given stimulant as Trypsin, hence any stimulant with similar behavior may be suitable for embodiments the present invention.

Cell Stimulation by Toxin

The present invention may also utilize any other suitable components as stimulant, for instance toxins. In this particular example, Alpha toxin may be used. Alpha toxin is produced by Staphylococcus aureus, discovered in 1880 by Ogston and named by Rosenbach in 1884. The name 'aureus' was chosen after the Latin word 'aurum' due to the gold-like pigmented colonies of the bacteria.

The toxin is a hydrophilic molecule with molecular weight ($M_r$) of 33,400 and is able to form pores in lipid bilayers. The mechanism of pore formation is a two-step process. In the first step toxin monomers bind to the membrane followed by hexamerization due to collisions during lateral diffusion in the bilayer. Each toxin molecule contains two domains, α and β, that display affinity for each other. The oligomerization process, which occurs spontaneously, ends when ring-structured hexamers are formed in which all α and β domains are mutually occupied. Toxin hexamers are relatively thick-walled cylinders, approximately 4 nm high and 10 nm wide, harboring a central pore of 1 to 2 nm in effective diameter.

At low concentrations, below 2 nM, the toxin binds exclusively to specific sites while at high concentrations, above 200 nM, the toxin binds to the membrane via a non-specific, absorption mechanism. But not every cell is equally sensitive to the effects of alpha toxin. For example the membranes of human granulocytes exposed to relatively high toxin doses (20 μg/ml, microgram per milliliter) did not show any pores.

The toxin is very stable over a wide pH range and soluble in aqueous solutions. Neither storage nor transport present a problem, as the toxin can be kept for several weeks at room temperature and even for several years at −20° C. Changing temperature between 0° C. and 37° C. only affects the kinetics of the reaction, leaving the activity of the toxin intact.

In a particular example of embodiments of the present invention, alpha toxin is applied to a white blood cell. FIG. 11 illustrates the Fc of white blood cells after alpha toxin incubation. The dashed line indicates the native Fc value.

The present invention is not limited to a particular toxin, and any suitable toxin may be used. As a particular example, Streptolysin-O may be used. Streptolysin-O (SLO) is a prototype of the cholesterol-binding family of bacterial exotoxins and is capable of forming large pores in the plasma membrane of mammalian cells. It is a water-soluble molecule of $M_r$ 69,000 and is produced by most strains of the β-hemolytic group A streptococci, the major pathogens of the genus *Streptococcus.*

After binding to a cholesterol-containing membrane, the toxin monomers diffuse laterally in the bilayer and oligomerize to form aggregates. This self-association results in the appearance of small arcs comprising very few subunits that insert into the membrane. The arc-shaped structures are hydrophylic at the concave side making the membrane lipids retract resulting in a crescent shape membrane defect. These structures are subsequently extended by successive addition of membrane bound SLO monomers to the free ends of the arc, eventually giving rise to the complete ring-shaped transmembrane pore. The rings are made of an estimated 50-80 SLO subunits and can reach a diameter of 35 nm.

In yet another example, MCF-7 cells were treated with alpha toxin at different concentrations (0.01, 0.1, 1 and 10 μg/ml, micrograms per milliliter). FIG. 10 shows the effect of the 10 μg/ml (micrograms per milliliter) concentration of alpha toxin. No distinct differences between the effects of other concentrations of alpha toxin on MCF-7 cells and PBMCS were observed. In this particular example, Alpha toxin has opposite effect in the different cells on which it is applied: Alpha toxin increases the crossover frequency of MCF-7 cells while it decreases the crossover frequency of PBMCS. Especially the decrease of the average Fc of PBMCS is pronounced as the Fc drops below the native Fc of MCF-7 cells. The Fc of the cells does not return to the native value either. In other words, the electrical cell membrane property was permanently changed by the Alpha-toxin. Noteworthy is that it takes around 20 minutes for PBMCS to display the full effect of alpha toxin while the effect on MCF-7 cells can already be observed after 5 minutes. Thus, according to embodiments of the present invention, monitoring the trend and time constant of cell recovery from Alpha-toxin stimulation can be used to distinguish tumor cells and WBCs.

The effect of SLO on the Fc of MCF-7 cells and WBCs is shown in FIG. 12. According to the diagram shown on the upper figure in FIG. 12, Fc vs effect SLO on MCF-7, the higher the dose, the bigger the change in the Fc. The same finding as Alpha-toxin stimulation was also found for SLO: in the effect of SLO on MCF-7, the recovered Fc increases higher than the native Fc for tumor cells while in the graph of the white blood cells after SLO, shown in the lower figure in FIG. 12 (for 10 microliters/milliliter as before), the recovered Fc drops to a lower value than the native Fc for WBCs. In other words, the electrical cell membrane property was permanently changed by the Alpha-toxin. According to embodiments of the present invention, the trend of Fc recovery can be used for cancer cell and WBC differentiation. The recovery time constant is comparable between cancer cells and WBCs.

Impact on Cell Membrane Capacitance

The impact of stimulation on cell membrane capacitance was shown in FIG. 13. The incubation of toxin significantly lowered the cancer cell membrane capacitance, while increased that of WBCs.

These methods and device can be combined according to each particular case, with a normal optimization of electric frequency, concentration, and in certain cases, also conductance of fluid. The chosen parameters may serve for measuring impedance (directly, or via conductance and capacitance) and crossover frequency, for instance for cell determination using look-up tables or even cell sorting using a microcontroller. These methods may be applied in a device according to embodiments of the present invention.

The invention claimed is:

1. A method for identifying a cell, the method comprising:
- providing a cell in a fluid with a predetermined electrical conductivity;
- stimulating the cell with a stimulant thereby modifying a cell membrane impedance of the cell; thereafter
- monitoring the cell membrane impedance by measuring a cross-over frequency of the cell by
  - applying at least one electrical field characterized by at least one non-zero frequency which creates a dielectrophoretic force on the cell,
  - measuring the dielectrophoretic force on the cell, and
  - determining a cross-over frequency of the cell, wherein the cross-over frequency is the frequency at which cell experiences zero DEP force;
- repeating the measurement of the crossover frequency of the cell for at least one fluid with a different electrical conductivity to determine a membrane capacitance density and a membrane conductance density; and
- identifying the cell based on the monitored cell membrane impedance, the monitored cell membrane impedance including the membrane capacitance density and the membrane conductance density.

2. The method according to claim 1, wherein applying at least one electrical field characterized by at least one non-zero frequency comprises varying the frequency of the electrical field.

3. The method according to claim 1, wherein applying at least one electrical field characterized by at least one non-zero frequency comprises applying electrical fields with different frequencies.

4. The method according to claim 1, wherein monitoring the cell membrane impedance comprises performing a direct electrical impedance measurement.

5. The method according to claim 1, wherein identifying the cell based on the monitored cell membrane impedance comprises correlating the monitored cell membrane impedance with predetermined cell membrane impedance measurements of a cell.

6. A method for sorting cells, the method comprising:
- providing a fluid comprising at least one cell;

identifying a type or subtype of the at least one cell using the method according to claim 1;

sorting the at least one cell based on the identified type or subtype.

7. The method according to claim 1, wherein the method further comprises:

providing a micro-fluidic device comprising:
- at least one inlet;
- at least one outlet; and
- a micro-fluidic channel comprising a plurality of electrodes positioned along the micro-fluidic channel, one end of the micro-fluidic channel being connected to the at least one inlet and the other end of the micro-fluidic channel being connected to the at least one outlet;
- wherein the plurality of electrodes comprises at least two groups of electrodes; and
- wherein each group of electrodes is connectable to at least one electric power supply unit capable of providing at least one voltage, of at least one non-zero frequency,
- wherein the monitoring the cell membrane impedance is performed using one or more of the groups of electrodes while the cell is in the micro-fluidic channel.

8. The method according to claim 7, wherein the micro-fluidic device further comprises a processing unit suitable for performing a correlation between the monitored cell membrane impedance and pre-defined cell membrane impedance models, and wherein the method further comprises identifying the cell based on the monitored cell membrane impedance comprises correlating the monitored cell membrane impedance with predetermined cell membrane impedance measurements of a cell.

9. The method according to claim 7, wherein the micro-fluidic channel features a meander-like shape.

10. The method according to claim 1, wherein the stimulant is a digestive enzyme, a toxin, or a surfactant.

11. The method according to claim 1, wherein the stimulant is a membrane pore-forming toxin.

12. The method according to claim 1, wherein monitoring the cell membrane impedance is performed by performing a plurality of cell membrane impedance measurements as a function of time or a continuous impedance measurement over a period of time.

13. The method according to claim 1, wherein the cell is a cancer cell.

14. The method according to claim 1, wherein the cell is a cell from a blood sample.

15. The method according to claim 1, wherein the stimulant is a digestive enzyme, a toxin, or a surfactant; and the cell is a cancer cell from a blood sample.

16. The method according to claim 7, wherein the stimulant is a digestive enzyme, a toxin, or a surfactant; and the cell is a cancer cell from a blood sample.

* * * * *